(12) United States Patent
Rogers et al.

(10) Patent No.: US 8,134,706 B2
(45) Date of Patent: Mar. 13, 2012

(54) MONITOR FOR MONITORING PARTICLES FLOWING IN A STACK

(75) Inventors: John Rogers, Little Eversden (GB); Michael Rigby, Ramsey (GB)

(73) Assignee: PCME Limited, Cambridgeshire (GB)

( * ) Notice: Subject to any disclaimer, the term of this patent is extended or adjusted under 35 U.S.C. 154(b) by 946 days.

(21) Appl. No.: 11/883,565

(22) PCT Filed: Feb. 2, 2006

(86) PCT No.: PCT/GB2006/000367
§ 371 (c)(1), (2), (4) Date: May 14, 2008

(87) PCT Pub. No.: WO2006/082417
PCT Pub. Date: Aug. 10, 2006

(65) Prior Publication Data
US 2011/0134427 A1    Jun. 9, 2011

(30) Foreign Application Priority Data
Feb. 2, 2005   (GB) .................................. 0502150.6

(51) Int. Cl.
*G01N 21/00*  (2006.01)
(52) U.S. Cl. ........................................ 356/338; 356/342
(58) Field of Classification Search ........... 356/335–344
See application file for complete search history.

(56) References Cited

U.S. PATENT DOCUMENTS

| | | | |
|---|---|---|---|
| 3,880,526 A | | 4/1975 | Kobayashi et al. |
| 4,040,749 A | * | 8/1977 | David et al. ..................... 356/437 |
| 4,126,396 A | * | 11/1978 | Hartmann et al. ............ 356/434 |
| 4,247,205 A | | 1/1981 | Typpo |
| 4,247,783 A | | 1/1981 | Pavlov |
| 4,249,244 A | * | 2/1981 | Shofner et al. ................. 250/573 |
| 4,361,403 A | | 11/1982 | Loos |

(Continued)

FOREIGN PATENT DOCUMENTS

EP   0271809   6/1988

(Continued)

OTHER PUBLICATIONS

GB Patent Office Search Report; Mar. 31, 2005 for Appln. GB 0502150.6.

(Continued)

*Primary Examiner* — Gregory J Toatley
*Assistant Examiner* — Jarreas C Underwood
(74) *Attorney, Agent, or Firm* — Abelman, Frayne & Schwab

(57) ABSTRACT

An instrument (10) for monitoring particles (67) flowing in a stack, includes: (a) a light source for providing a light beam (60); (b) a sensor/and (c) a probe housing. The housing comprises: (i) a mount (25); (ii) a proximal portion (30) including a first aperture (35) through which in use the light beam (60) exits; (iii) a distal portion (50), including a second aperture (55) through which the light beam (60) enters after having been scattered from particles (67) flowing in the stack, and a focusing mirror (70) arranged to reflect and focus the scattered light (90); (iv) a medial portion (40), connecting the distal portion (50) to the proximal portion (30); (v) a waveguide (80), passing from the distal portion (50) through the medial portion (40) and the proximal portion (30) to the sensor and arranged to guide to the sensor the light (90) reflected and focused by the focusing mirror (70).

29 Claims, 2 Drawing Sheets

U.S. PATENT DOCUMENTS

| | | | |
|---|---|---|---|
| 4,482,247 A * | 11/1984 | Meltz et al. | 356/343 |
| 4,497,577 A | 2/1985 | Sato et al. | |
| 4,555,627 A * | 11/1985 | McRae, Jr. | 250/334 |
| 5,009,064 A * | 4/1991 | Grob et al. | 60/276 |
| 5,028,790 A | 7/1991 | McGowan et al. | |
| 5,067,814 A | 11/1991 | Suzuki et al. | |
| 5,269,937 A | 12/1993 | Dollinger et al. | |
| 5,305,073 A | 4/1994 | Ford, Jr. | |
| 5,418,615 A * | 5/1995 | Doyle | 356/436 |
| 6,157,692 A * | 12/2000 | Christensen et al. | 377/10 |
| 6,936,828 B2 * | 8/2005 | Saccomanno | 250/458.1 |

FOREIGN PATENT DOCUMENTS

| | | |
|---|---|---|
| EP | 0848243 | 6/1998 |
| GB | 2390893 | 1/2004 |
| JP | 58206948 | 2/1983 |
| WO | WO 83/04098 | 11/1983 |
| WO | WO 2004/008117 | 1/2004 |

OTHER PUBLICATIONS

European Patent Office: International Search Report and Written Opinion; May 12, 2006 for International Patent Application No. PCT/GB2006/000367.

European Patent Office Search Report; Nov. 10, 2005, Application EP 03 76 4014.

GB Patent Office Examination Report Dated Jan. 27, 2005, Application GB0216381.4.

* cited by examiner

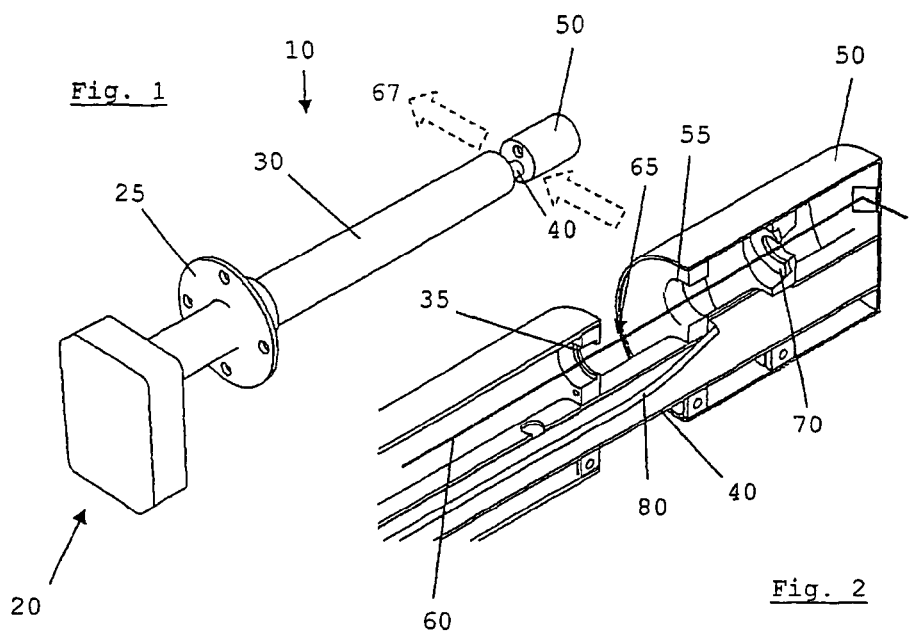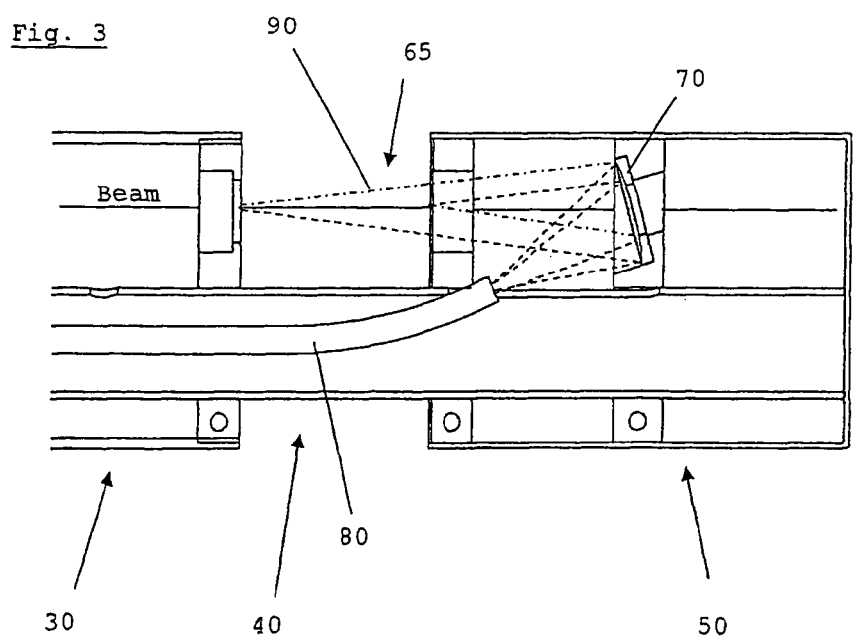

MONITOR FOR MONITORING PARTICLES FLOWING IN A STACK

I. BACKGROUND AND FIELD OF THE INVENTION

This invention relates to the field of monitoring particles flowing in a stack.

When light interacts with particles, the particles may reflect, refract, diffract or absorb the light, the nature of the interaction depending on the size, refractive index and surface profile of the particles and the wavelength of the interacting light.

For objects that are small compared with the wavelength of the light, the light will undergo Rayleigh scattering and a proportion of the light may be redirected in all directions. As the object size increases such that it is comparable to the wavelength of the light a larger proportion of the scattered light is redirected in the forward direction within well-defined angular lobes. This phenomenon is known as forward light scattering or Mie scattering. As the object size increases still further such that it is much greater than the wavelength of light, classical geometric optics begin to dominate.

The light scattering approach to dust measurement brings with it problems associated with reliable discrimination between scattered light and stray light or residues from the incident beam. Particle monitoring systems are installed in many dirty processes and hence contamination of optical surfaces is an important issue. Similarly, calibration of existing monitoring systems does not optimally take into account the effects of contamination. Contamination of optical surfaces of the monitor itself may produce unwanted scattered light that is measured by the monitor, giving a false reading. As discussed above, particles of different size scatter light in different directions and so the amount of light received by a prior-art probe depends on the size of particles in the flow, as well as their number and mass density; that can lead to errors in measurement. Prior-art monitors use relatively short interaction lengths but short interaction lengths make measurements vulnerable to local inhomogeneities in the particle flow. Readings from prior-art monitors may be affected by the harsh conditions that are prevalent in many stacks. For example, probes using glass-fibres are unsuitable for operation above 350° C.-400° C. due to temperature limitations of the fibre cladding and fibres based on sapphire, which may be able to operate at those temperatures, are very expensive. A particular disadvantage of some prior art designs is that, although they provide mechanisms for checking the calibration of a probe, they do so by moving one or more parts of the system that is to be calibrated in a way that may cast doubt on the reliability of the calibration measurements.

International Patent Application No. PCT/GB2003/003073 (published as WO 2004/008117) describes a particle monitor for, monitoring particles flowing in a stack. A light source generates a measurement beam on a first side of the particle flow. The measurement beam is directed by an optical system towards the opposite side of the particle flow without the measurement beam being scattering from the particles. On that opposite side of the flow, a reflector reflects the measurement beam back towards the first side of the particle flow, via an optical system that directs the measurement beam into the particle flow. Light from the measurement beam is thereby scattered by the particles and the scattered light is detected by a detector on the first side of the particle flow. The instrument described in that International Patent Application has the advantage that it provides a contamination and calibration check that does not involve moving any parts of the system that is to be calibrated, which enhances the reliability of the calibration measurements. However, we have found that the instrument suffers from some significant problems.

II. OBJECTS AND SUMMARY OF THE NEW INVENTION

An object of the invention is to provide an improved particle detector that does not suffer or suffers to a reduced extent from problems found in prior-art detectors. According to a first aspect of the invention there is provided an instrument for monitoring particles flowing in a stack, comprising:

(a) a light source for providing a light beam;
(b) a sensor; and
(c) a probe housing comprising:
  (i) a mount for fixing the housing to a wall of the stack;
  (ii) a proximal portion, closer to the mount and arranged to project into the stack in use, including a first aperture through which in use the light beam exits from the proximal portion;
  (iii) a distal portion, further from the mount, comprising a second aperture through which in use light from the light beam enters the distal portion after having been scattered from particles flowing in the stack, and a focusing mirror arranged to reflect and focus the scattered light;
  (iv) a medial portion, connecting the distal portion to the proximal portion so that there is a space between the proximal and distal portions, in which the scattering occurs; and
  (v) a waveguide, passing from the distal portion through the medial portion and the proximal portion to the sensor and arranged to guide to the sensor the light reflected and focused by the focusing mirror.

We have found that instruments according to the invention perform significantly better than the instrument described in WO 2004/008117. In particular, the present invention requires significantly fewer optical surfaces than are taught in the WO 2004/008117 instrument. We have found that two particular benefits result from a reduction in the number of optical surfaces. First, the alignment of elements within the instrument is more robust and so fewer recalibrations are needed. Second, sensitivity to the effects of contamination is reduced.

The light source may be a laser. The sensor may be a large-area photodiode. Preferably, the first and second apertures are holes; however, the first and/or second aperture may alternatively be a glazed window; in that case it is preferable to provide an external air purge for each window.

Advantageously, when the instrument is installed in a stack, the light source and/or sensor are positioned outside the stack whereas the distal housing portion (including the focusing mirror) is arranged inside the stack. The light source and the sensor may be positioned on the same side of the stack as each other, preferably adjacent to each other. The light source and sensor may be contained in an external housing. When the instrument is installed in a stack, the mount may be arranged such that the probe housing projects into the interior of the stack and the external housing is outside the wall of the stack. The focusing mirror may be arranged to reflect and focus light scattered at angles between 3° and 17° from the direction of the unscattered light beam.

The focusing mirror may be arranged to reflect and focus light scattered at angles between 4° and 16° from the direction of the unscattered light beam. The focusing mirror may be arranged to reflect and focus light scattered at angles between 7° and 12° measured from the midpoint of the measurement volume. The focusing mirror may be arranged to reflect and focus light scattered at angles between 8° and 11°/measured from the midpoint of the measurement volume.

The waveguide may be a rigid rod (as opposed to a flexible fibre), which may be a glass rod, for example a quartz rod. We have found use of a rigid rod is advantageous over use of, for example, an optical fibre; we have found using a focusing mirror in combination with a waveguiding rod to be particularly advantageous. Although an optical fibre may be curved round so that scattered light could be coupled directly into it without a need for a mirror, the combined effect of the larger acceptance angle and cross-sectional area of the rod and the large collecting cross-section of the mirror allows a significantly larger amount of the scattered light to be coupled into the waveguide, which advantage outweighs the disadvantage of having to use a second optical component (the mirror). Moreover, as discussed above, clad glass fibres are not suitable for use at the high temperatures usually found in stacks. Preferably, the rod is suitable for use in the instrument at temperatures greater than 350 C, more preferably temperatures greater than 400° C.

The rod may have a diameter of between 4 mm and 12 mm. A heat-absorbing filter may be provided at the end of the waveguide nearest to the sensor. Such a filter reduces the amount of infra-red reaching the sensor; such a reduction is particularly desirable in a stack where infra-red emissions from hot surfaces (including particles) may overwhelm scattered measurement light.

The waveguide may be substantially straight with a curved distal portion positioned in the medial or distal portions of the housing, and pointing towards the focusing mirror; that arrangement increases coupling of light into the waveguide from the focusing mirror. The focusing mirror may have a radius of curvature of between 10 mm and 150 mm, preferably between 25 mm and 100 mm. The proximal, medial and distal portions may be tubes, which may be of circular cross-section.

The focusing mirror may include a hole through which light from the light beam that has not been scattered by the particles passes. That residual unscattered light may be absorbed in a beam dump comprised in the distal portion of the probe housing.

The proximal portion of the probe housing may include an iris that is adjustable to reduce the amount of stray light from the main beam reaching the focusing mirror, and hence reaching the sensor via the waveguide. A plurality of irises may be provided in the proximal portion.

The instrument may further comprise a purge airflow arranged adjacent to the first and/or second aperture. The instrument may further comprise a diffuser arranged to be rotated into the path of the light beam within the proximal portion of the housing. A plurality of such filters may be provided. Contamination and linearity checks can be performed using one or more diffuser, which are rotated into the path of the light beam behind the first aperture, to produce known scattering signals.

According to a second aspect of the invention there is provided an instrument for monitoring particles flowing in a stack, comprising:
(a) a light source for providing a light beam;
(b) a sensor; and
(c) a probe housing, arranged to project into the particle flow and comprising:
  (i) a scattering zone, where light from the light source scatters from the flowing particles;
  (ii) a reflector arranged on the opposite side of the scattering zone from the light source;
  (iii) a waveguide arranged to guide scattered light from the reflector to the sensor; wherein, in use, the light beam passes from the light source, through the probe housing to the scattering zone, and light scattered from the light beam in the scattering zone is reflected by the reflector into the waveguide and guided by the waveguide to the sensor where it is detected.

According to a third aspect of the invention, there is provided an instrument for monitoring particles flowing in a stack, comprising:
(a) a light source for providing a light beam, and a sensor for detecting light scattered in a scattering zone from the light beam by the flowing particles, the light source and the sensor being arranged on a first side of the scattering zone;
(b) a waveguide arranged to guide the scattered light to the sensor;
(c) a reflector on a second, opposite side of the scattering zone, the reflector being arranged to reflect the scattered light from the scattering zone into the waveguide.

An instrument according to any aspect of the invention may comprise any of the features described in respect of any other aspect of the invention.

According to a fourth aspect of the invention there is provided a stack installation including an instrument according to the first, second or third aspect of the invention.

According to a fifth aspect of the invention, there is provided a method of monitoring particles flowing in a stack, comprising:
(a) passing a light beam from a light source to a scattering zone, where light is scattered from particles flowing through the light beam;
(b) reflecting the light scattered from the light beam into a waveguide;
(c) guiding the scattered light through the waveguide to a sensor;
(d) detecting the scattered light.

The invention also provides use of a waveguide in such a method.

Preferably, the waveguide is a rigid rod. The rod may be a glass rod. The rod may have a diameter of between 4 mm and 12 mm.

The method may further comprise passing the scattered light through a heat-absorbing filter prior to detecting the scattered light.

Preferably, the light is reflected from a curved mirror and focused by the mirror into the waveguide. The waveguide may be a substantially straight rod with a curved end portion. The curved end portion may be arranged to point towards the focusing mirror.

The curved mirror includes a hole through which unscattered light from the light beam passes.

The method may comprise use of an instrument according to any other aspect of the invention or of any of the features described above in respect of any aspect of the invention.

III. BRIEF DESCRIPTION OF THE DRAWINGS

An embodiment of the invention will now be described, by way of example only, with reference to the accompanying figures, of which:

FIG. 1 is a perspective view of an instrument according to the invention;

FIG. 2 is a cut-away view of part of a proximal portion, a medial portion and a distal portion of the instrument of FIG. 1;

FIG. 3 is a cross-sectional view corresponding to FIG. 2, showing scattering of light between the proximal housing portion and the distal housing portion;

IV. DETAILED DESCRIPTION OF THE PREFERRED EMBODIMENTS

Figure 4:
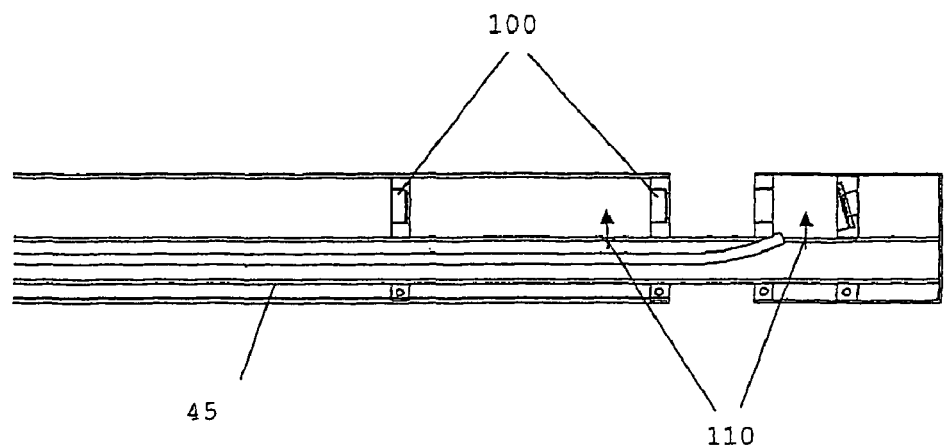
FIG. 4 is a further cross-sectional view of the instrument of FIG. 1, showing in particular internal features of the proximal and distal housing portions.

An example of an instrument 10 according to the invention (FIG. 1) comprises an external housing 20, containing a laser and a large-area photodiode (not shown) and a probe housing comprising a proximal portion 30, a medial portion 40 and a distal portion 50, which are cylindrical metal tubes, of circular cross-section. The proximal and distal housing portions are of the same diameter. The medial portion 40 joins the distal portion to the medial portion and is of a smaller diameter.

The instrument also comprises mount 25, which is a plate of circular cross-section, which surrounds the proximal portion 30 and is arranged to be bolted onto the wall of a stack. When instrument 10 is mounted in a stack, external housing 20 is positioned outside the stack wall, out of the harsh environment in which particles are flowing, whereas the distal (50), medial (40) and at least part of the proximal (30) housing portions project into the stack, the medial portion being well inside the particle flow, so as to enable reliable readings of flow rates or the like with reduced influence from the flow effects associated with the walls of the stack.

The laser produces a beam 60 which travels from external housing 20, through proximal housing portion 30, out of first aperture 35 and into scattering volume 65 (FIG. 2). Scattering volume 65 is the space, between proximal housing portion 30 and distal housing portion 50, resulting from the reduced diameter of medial portion 40.

Particle flow 67, the properties of which are to be measured by the instrument, flows through scattering volume 65. When beam 60 impinges on the particles, light is scattered at angles that depend inter alia on the size, of the particles. Forward-scattered light passes into distal portion 50 through second aperture 55.

In distal portion 50, scattered light 90 falls on mirror 70 (FIG. 3). Mirror 70 is a curved mirror having a radius of curvature of 50 mm. Light scattered at angles between 3.8° and 16.4 from the direction of the main beam 60 (corresponding to between 7.7° and 11.4°, measured from the midpoint of the measurement volume) is incident on mirror 70 and is reflected and focused by mirror 70 into an end of a waveguide 80. The proximal and distal ends of the volume in which the beam 60 impinges on the particle flow 67 define the maximum and minimum angles detected by instrument 10.

Mirror 70 has a 17 mm diameter hole at its centre. Light from beam 60 that is not scattered by the particle flow (or that is scattered at less than 4°) passes through that hole and is redirected into a beam dump, where it is absorbed.

Figure 5:
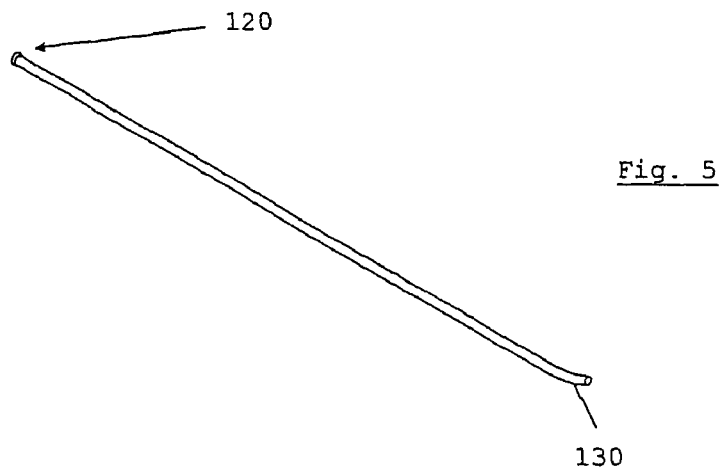
FIG. 5 is a perspective view of a waveguide found in the instrument of FIG. 1.

Waveguide 80 (FIG. 5) is a quartz rod of 8 mm diameter. It runs from just inside the distal housing portion 50, through the interior of medial portion 40, and proximal portion 30 to the sensor in housing 20. Waveguide 80 is curved at its end 130 closest to mirror 70, so that end 130 points towards mirror 70, and can be positioned to face directly into the reflected scattered light increasing the amount of light coupled into the waveguide. For the rest of its length, waveguide 80 runs parallel to the longitudinal axis of the probe housing.

At the other end of waveguide 80, closest to the sensor, a small heat-absorbing filter is provided which reduces the amount of infrared light (which is generally undesirable in these measurements) reaching the sensor.

Waveguide 80 runs inside an elongate tube 45, which runs along the length of the probe. Part of tube 45 forms medial housing portion 40; the rest runs inside distal portion 50 and proximal portion 30. As well as being a mechanical support within the instrument and a conduit for purged air, tube 45 serves to prevent stray light and, in the medial portion, particles from impinging on waveguide 80.

Two iris outlets 100 are provided (FIG. 4) within proximal housing portion 30. The irises are adjusted to allow most of beam 60 to pass into scattering volume 65 whilst reducing the amount of unwanted, stray light that can pass out of proximal housing portion 30.

Two air purges 110 are provided, one adjacent to aperture 35 and one adjacent to aperture 55. The purges 110 serve to reduce contamination of the optical surfaces of the instrument 10 by particles from the stack flow.

Figure 6:
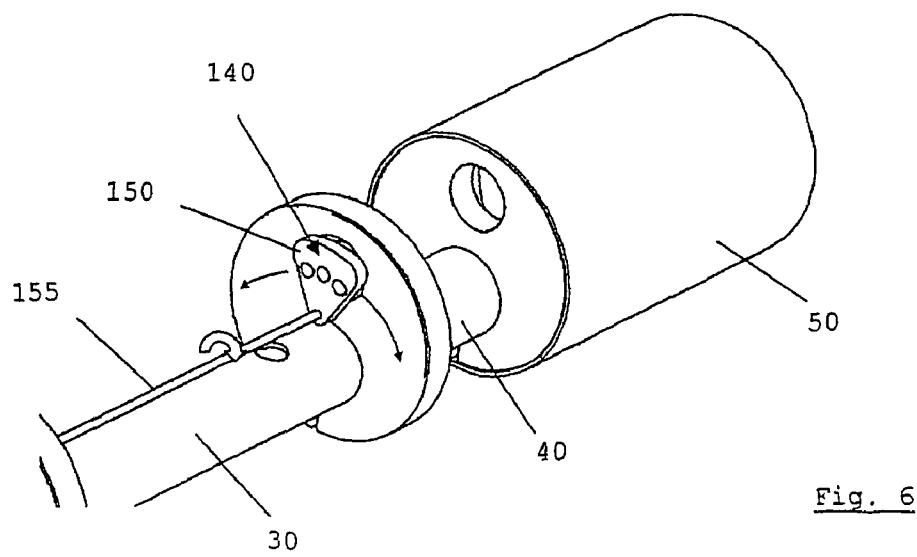
FIG. 6 is a perspective view showing further elements of the instrument of FIG. 1.

Despite such precautions, contamination of optical surfaces inevitably occurs over time. Regular checks are carried out to establish the extent of such contamination and to check that the instrument 10 remains calibrated. The checks are carried out using diffusers 140, which are mounted on a rotatable caddy 150 just inside proximal housing portion 30, between and close to the second of irises 100 (FIG. 6), such that the second iris 100 can be used to control the diffused beam without significantly reducing the maximum optical power available. Caddy 150 is swung across aperture 35 by rotation of rod 155. Three diffusers 140 are provided and can be selected by appropriate rotations of rod 155.

To check for contamination, a selected diffuser 140 is swung in front of aperture 35 and hence into the path of beam 60. Beam 60 is expanded by the diffuser and floods across scattering volume 65. The expanded beam dominates any scattering from particles in scattering volume 65, such that the overwhelming proportion of light reflected and focused by mirror 70 is diffused laser light, with scattered light rendered insignificant. If the optics between diffuser 140 and the sensor are substantially free from contamination, the signal detected by the sensor will be the same every time diffuser 140 is swung into beam 60. Conversely, if there is any reduction in the detected signal, that can be attributed to contamination of optical surfaces and, if the reduction is sufficiently severe to warrant it, the instrument can be removed from the stack and cleaned. Similarly, when it is desired to check the calibration and linearity of the instrument, the two other of diffusers 140 are placed alternately in beam 60. One diffuser is of relatively high neutral density (ND) and the other of relatively low ND, so respectively low and high amounts of light, which are known prior to installation of the instrument, reach the sensor when each diffuser is in place. By measuring those light levels, any necessary changes in the calibration of the instrument can be inferred.

Such a method of carrying out a contamination and calibration check is particularly advantageous because it is achieved without movement of any part of the instrument that is involved in normal measurement. Rather, the light diffused by diffusers 140 is incident on the same parts of mirror 70 and waveguide 80 as light scattered from the particle flow, and so the checks are made on the surfaces that are actually used in normal measurement.

While the invention has been described in conjunction with several embodiments, it is to be understood that many alternatives, modifications, and variations will be apparent to those skilled in the art in light of the foregoing description. Accordingly, this invention is intended to embrace all such alternatives, modifications, and variations which fall within the spirit and scope of the appended claims.

The invention claimed is:

1. An instrument for monitoring particles flowing in a stack, comprising:
   (a) a light source for providing a light beam;
   (b) a sensor; and
   (c) a probe housing comprising:
      (i) a mount for fixing the housing to a wall of the stack;
      (ii) a proximal portion, closer to the mount and arranged to project into the stack in use, including a first aperture through which in use the light beam exits from the proximal portion;
      (iii) a distal portion, further from the mount, comprising a second aperture through which in use light from the light beam enters the distal portion after having been scattered from particles flowing in the stack, and a focusing mirror arranged to reflect and focus the scattered light;
      (iv) a medial portion, connecting the distal portion to the proximal portion so that there is a space between the proximal and distal portions, in which the scattering occurs;
      (v) a waveguide, passing from the distal portion through the medial portion and the proximal portion to the sensor and arranged to guide to the sensor the light reflected and focused by the focusing mirror.

2. An instrument as claimed in claim 1, in which the first and second apertures are holes.

3. An instrument as claimed in claim 1, in which the focusing mirror is arranged to reflect and focus light scattered at angles between 3° and 17°, measured from the midpoint of the measurement volume.

4. An instrument as claimed in claim 1, in which the waveguide is a rigid rod.

5. An instrument as claimed in claim 4, in which the rod is a glass rod.

6. An instrument as claimed in claim 5, in which the rod has a diameter of between 4 mm and 12 mm.

7. An instrument as claimed in claim 1, in which the waveguide is substantially straight with a curved distal portion positioned in the medial or distal portions of the housing, and pointing towards the focusing mirror.

8. An instrument as claimed in claim 1, in which a heat-absorbing filter is provided at the end of the waveguide nearest to the sensor.

9. An instrument as claimed in claim 1, in which the focusing mirror includes a hole through which light from the light beam that has not been scattered by the particles passes.

10. An instrument as claimed in claim 1, in which the proximal portion of the probe housing includes an iris that is adjustable to reduce the amount of stray light from the main beam reaching the focusing mirror and hence the sensor via the waveguide.

11. An instrument as claimed in claim 1, which further comprises a diffuser arranged to be rotated into the path of the light beam within the proximal portion of the housing.

12. An instrument for monitoring particles flowing in a stack, comprising:
   (a) a light source for providing a light beam, and a sensor for detecting light scattered in a scattering zone from the light beam by the flowing particles, the light source and the sensor being arranged on a first side of the scattering zone;
   (b) a probe housing comprising:
      (i) a mount for fixing the housing to a wall of the stack;
      (ii) a proximal portion, closer to the mount and arranged to project into the stack in use, including a first aperture through which in use the light beam exits from the proximal portion;
      (iii) a distal portion, further from the mount, comprising a second aperture through which in use light from the light beam enters the distal portion after having been scattered from particles flowing in the stack, and a focusing mirror arranged to reflect and focus the scattered light;
      (iv) a medial portion, connecting the distal portion to the proximal portion so that there is a space between the proximal and distal portions, in which the scattering occurs;
      (v) a waveguide, passing from the distal portion through the medial portion and the proximal portion to the sensor and arranged to guide to the sensor the light reflected and focused by the focusing mirror.

13. An instrument as claimed in claim 12, in which the waveguide is a rigid rod.

14. An instrument as claimed in claim 13, in which the rod is a glass rod.

15. An instrument as claimed in claim 13, in which the rod has a diameter between 4 mm and 12 mm.

16. An instrument as claimed in claim 12, further comprising a heat-absorbing filter through which the scattered light passes prior to detection by the sensor.

17. An instrument as claimed in claim 12 further comprising a curved mirror from which the light is reflected and focused into the waveguide.

18. An instrument as claimed in claim 17 in which the waveguide is a substantially straight rod with a curved end portion.

19. An instrument as claimed in claim 18, in which the curved end portion points towards the focusing mirror.

20. An instrument as claimed in claim 17 in which the curved mirror includes a hole through which unscattered light from the light beam passes.

21. A method of monitoring particles flowing in a stack, comprising:
   (a) passing a light beam from a light source to a scattering zone using the instrument of claim 12, where light is scattered from particles flowing through the light beam;
   (b) reflecting the light scattered from the light beam into a waveguide;
   (c) guiding the scattered light through the waveguide to a sensor;
   (d) detecting the scattered light.

22. A method as claimed in claim 21, in which the waveguide is a rigid rod.

23. A method as claimed in claim 22, in which the rod is a glass rod.

24. A method as claimed in claim 22, in which the rod has a diameter between 4 mm and 12 mm.

25. A method as claimed in claim 21, further comprising passing the scattered light through a heat-absorbing filter prior to detecting the scattered light.

26. A method as claimed in claim 21 in which the light is reflected from a curved mirror and focused by the mirror into the waveguide.

27. A method as claimed in claim 26 in which the waveguide is a substantially straight rod with a curved end portion.

28. A method as claimed in claim 27, in which the curved end portion is arranged to point towards the focusing mirror.

29. A method as claimed in claim 26 in which the curved mirror includes a hole through which unscattered light from the light beam passes.

* * * * *